United States Patent
Hartfield et al.

(10) Patent No.: US 7,495,749 B2
(45) Date of Patent: Feb. 24, 2009

(54) RAPID METHOD FOR SUB-CRITICAL FATIGUE CRACK GROWTH EVALUATION

(75) Inventors: Cheryl Diane Hartfield, McKinney, TX (US); Darvin Renne Edwards, Garland, TX (US)

(73) Assignee: Texas Instruments Incorporated, Dallas, TX (US)

( * ) Notice: Subject to any disclaimer, the term of this patent is extended or adjusted under 35 U.S.C. 154(b) by 548 days.

(21) Appl. No.: 11/209,162

(22) Filed: Aug. 22, 2005

(65) Prior Publication Data
US 2007/0051437 A1 Mar. 8, 2007

(51) Int. Cl.
*G01B 11/16* (2006.01)
*G01N 29/04* (2006.01)
*G01L 1/24* (2006.01)

(52) U.S. Cl. ............... 356/32; 356/34; 73/799; 73/800; 73/801

(58) Field of Classification Search ............ 356/32, 356/34, 35, 35.5, 237.1
See application file for complete search history.

(56) References Cited

U.S. PATENT DOCUMENTS

| | | | | |
|---|---|---|---|---|
| 4,175,447 A | * | 11/1979 | Fukuhara | 73/799 |
| 4,593,565 A | * | 6/1986 | Chamuel | 73/601 |
| 4,710,030 A | * | 12/1987 | Tauc et al. | 356/432 |
| 5,438,402 A | | 8/1995 | Gupta | |
| 5,647,667 A | * | 7/1997 | Bast et al. | 374/57 |
| 5,838,446 A | * | 11/1998 | Meth et al. | 356/632 |
| 6,400,449 B2 | * | 6/2002 | Maris et al. | 356/72 |
| 6,759,659 B2 | * | 7/2004 | Thomas et al. | 250/341.6 |
| 7,057,176 B2 | * | 6/2006 | Rothenfusser et al. | 250/341.6 |
| 7,339,676 B2 | * | 3/2008 | Maris | 356/432 |
| 2004/0089812 A1 | * | 5/2004 | Favro et al. | 250/341.6 |

OTHER PUBLICATIONS

Mikel R. Miller and Michael C. Mello, "Laser Spallation Adhesion Metrology for Electronic Packaging Development", IEEE Electronic Components and Technology Conference, May 2002, (Copyrighted Paper).

Junlan Wang, Richard L. Weaver, Nancy R. Sottos, "A Parametric Study of Laser Induced Thin Film Spallation", Experimental Mechanics vol. 42, No. 1, Mar. 2002, pp. 74-83, Sage Publications, (Copyrighted Paper).

(Continued)

*Primary Examiner*—Roy M Punnoose
(74) *Attorney, Agent, or Firm*—Yingsheng Tung; Wade James Brady, III; Frederick J. Telecky, Jr.

(57) ABSTRACT

In a method and system for evaluating sub-critical fatigue crack growth in a semiconductor device, a plurality of energy pulses generated by an energy source are repeatedly impinged onto the semiconductor device for a predefined time interval. The repeated impinging of the plurality of energy pulses induces a mechanical stress within the semiconductor device. The induced mechanical stress, maintained below a threshold and repeated for a predefined number of cycles, causes a formation of a sub-critical fatigue crack within the semiconductor device. A detector detects the presence of the sub-critical fatigue crack leading to a fatigue failure. A rapid determination of a pass or fail status for a fatigue test of the semiconductor device is made by comparing a total number of cycles to fatigue failure to a predefined benchmark.

20 Claims, 1 Drawing Sheet

OTHER PUBLICATIONS

Vijay Gupta, Vassili Kireev, Jun Tian, Hiroshi Yoshida and Haruo Akahoshi, "Glass-Modified Stress Waves For Adhesion Measurement Of Ultra Thin Films For Device Applications", Journal of the Mechanics and Physics of Solids, vol. 51, Issue 8, Aug. 2003, pp. 1395-1412 (Copyrighted Paper).

Ikeda, et al., "AE Monitoring From CVD-Diamond Film Subjected To Micro-Indentation And Pulse Laser Spallation", DGZfP-Proceedings BB 90-CD, Lecture 25, 26th European Conference on Acoustic Emission Testing (EWGAE 2004), pp. 273-280.

Junlan Wang, Nancy R. Sottos, Richard L. Weaver, "Tensile And Mixed-Mode Strength Of A Thin Film-Substrate Interface Under Laser Induced Pulse Loading", Journal of the Mechanics and Physics of Solids, vol. 52, Issue 5, May 2004, pp. 999-1022.

* cited by examiner

RAPID METHOD FOR SUB-CRITICAL FATIGUE CRACK GROWTH EVALUATION

BACKGROUND

The present disclosure relates generally to the testing of integrated circuits (ICs), and more particularly to an improved technique for evaluating sub-critical fatigue crack growth in semiconductor devices.

Sub-critical fatigue crack growth generally refers to a phenomenon occurring in materials where microscopic flaws that may be statistically distributed within the material may extend as cracks even under low stress levels. The material when subjected to a repeated stress, which may be constant and/or fluctuating, may fracture and eventually fail due to fatigue. Fatigue induced fractures are typically progressive and grow under the action of the repeated stress. Sub-critical fatigue crack growth is one of the major failure mechanisms of semiconductor and packaging materials used in the fabrication of the semiconductor devices, thereby resulting in reduced reliability and higher costs.

Presently, testing of samples to detect and analyze sub-critical fatigue crack growth is a time intensive process, often taking several days or longer to test one sample. For example, fatigue tests are performed with samples having specific geometry in bending-beam based mechanical tests, such as 4-point bend testing and double cantilever beam testing (DCB). Mechanical stress is repeatedly applied in cycles, such that it may take several hours to test one strip of a multi-strip sample set. All strips are typically measured and averaged to produce a value for that one sample set. As such, testing for sub-critical fatigue crack growth has been generally performed in an academic environment, or applied in industry on a limited basis for materials characterization during new material implementation. It is impractical to apply on a wide basis for routine process characterization and process control.

Recently, laser spallation based adhesion testing techniques have been suggested and are described in further detail in the following United States patent and technical papers, which are hereby incorporated herein by reference into this specification: 1) U.S. Pat. No. 5,438,402, entitled "System And Method For Measuring The Interface Tensile Strength Of Planar Interfaces", Gupta, 2) "Laser Spallation Adhesion Metrology for Electronic Packaging Development", Mikel R. Miller and Michael C. Mello, IEEE Electronic Components and Technology Conference, May 2002, (Copyrighted Paper), 3) "A Parametric Study of Laser Induced Thin Film Spallation", Junlan Wang, Richard L. Weaver, Nancy R. Sottos, Experimental Mechanics Vol. 42, No. 1, March 2002, pages 74-83, Sage Publications, (Copyrighted Paper), 4) "Glass-Modified Stress Waves For Adhesion Measurement Of Ultra Thin Films For Device Applications", Vijay Gupta, Vassili Kireev, Jun Tian, Hiroshi Yoshida and Haruo Akahoshi, Journal of the Mechanics and Physics of Solids, Volume 51, Issue 8, August 2003, Pages 1395-1412 (Copyrighted Paper), 5) "AE Monitoring From CVD-Diamond Film Subjected To Micro-indentation And Pulse Laser Spallation", Ikeda, et al., DGZfP-Proceedings BB 90-CD, Lecture 25, 26th European Conference on Acoustic Emission Testing (EWGAE 2004), pages 273-280, and 6) "Tensile And Mixed-Mode Strength Of A Thin Film-Substrate Interface Under Laser Induced Pulse Loading", Junlan Wang, Nancy R. Sottos, Richard L. Weaver, Journal of the Mechanics and Physics of Solids, Volume 52, Issue 5, May 2004, pages 999-1022. However, traditional laser spallation techniques for testing adhesion properties between two planar interfaces may not be applicable to test and analyze sub-critical fatigue crack growth in semiconductor and packaging materials.

SUMMARY

A need exists to provide an improved method and system for testing and analysis of sub-critical fatigue crack growth in semiconductor devices. Specifically, there is a need for performing a rapid test for evaluating sub-critical fatigue crack growth, thereby making the test deployable in a semiconductor manufacturing environment. Accordingly, it would be desirable to provide an efficient method and system for fatigue testing, absent the disadvantages found in the prior techniques discussed above.

The foregoing need is addressed by the teachings of the present disclosure, which relates to an improved method and system for testing semiconductor devices. According to one embodiment, in a method and system for evaluating sub-critical fatigue crack growth in a semiconductor device, a plurality of energy pulses generated by an energy source are repeatedly impinged onto the semiconductor device for a predefined time interval. The repeated impinging of the plurality of energy pulses induces a mechanical stress within the semiconductor device. The induced mechanical stress maintained below a threshold and repeated for a predefined number of cycles causes a formation of a sub-critical fatigue crack within the semiconductor device. A detector detects a presence of the sub-critical fatigue crack leading to a fatigue failure. A rapid determination of a pass or fail status for a fatigue test of the semiconductor device is made by comparing a total number of cycles to fatigue failure to a predefined benchmark.

In one aspect of the disclosure, a method of testing a semiconductor device includes fatiguing a selective portion of the semiconductor device by repeatedly impinging a plurality of energy pulses onto the selective portion. The plurality of energy pulses are generated by an energy source such as a Nd:YAG laser. A mechanical stress is induced within the semiconductor device due to the repeated impinging of the plurality of energy pulses. The mechanical stress induced is controlled to be below a threshold by adjusting amplitude and duration of the plurality of energy pulses. The mechanical stress causes a formation of a sub-critical fatigue crack, which is detected by a detector. The growth of the sub-critical fatigue crack due to the repeated number of cycles leads to a fatigue failure. A rapid determination of a pass or fail status for a fatigue test of the semiconductor device is made by comparing a total number of cycles to fatigue failure to a predefined benchmark.

Several advantages are achieved by the method and system for testing semiconductor devices according to the illustrative embodiments presented herein. The embodiments advantageously provide for a rapid test for evaluating sub-critical fatigue crack growth, thereby making the test deployable in a semiconductor manufacturing environment for purposes of material selection, development, and optimization; process control; and failure analysis and root cause investigation, among other possibilities. This advantageously enables manufacturers of ICs to detect and replace defective ICs in a timely and cost effective manner, thereby improving product reliability.

DETAILED DESCRIPTION

Figure 1:
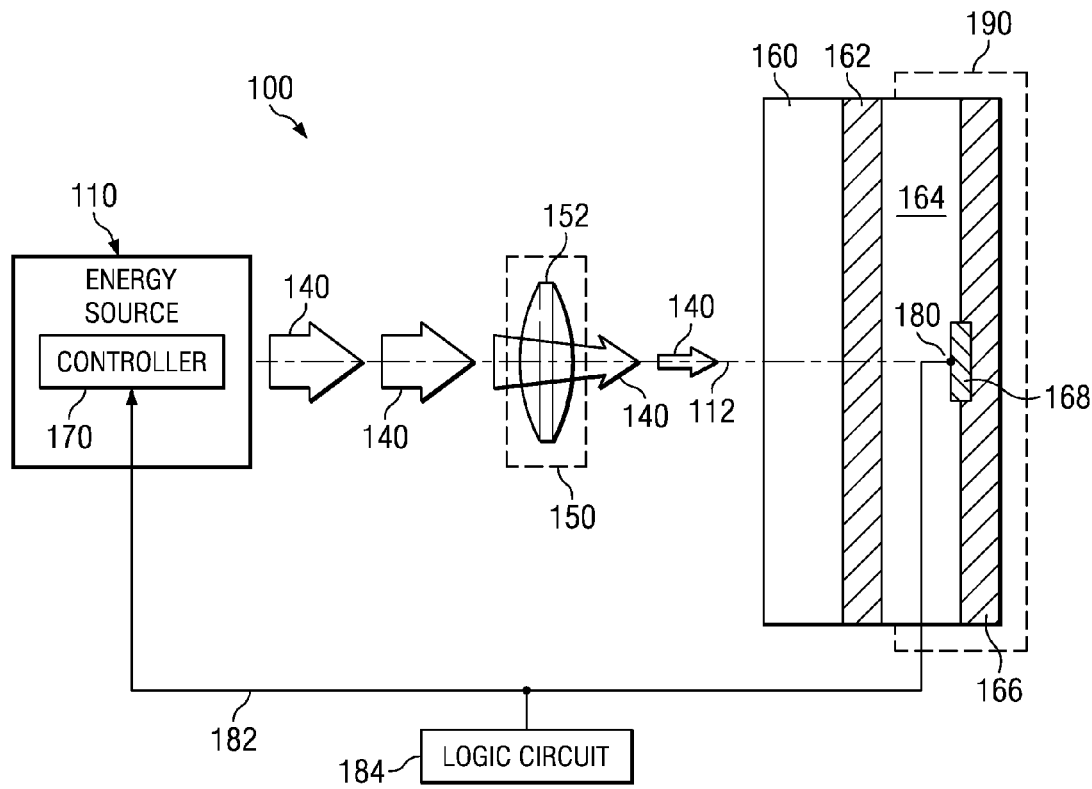
FIG. 1 illustrates a block diagram of a fatigue test system, according to an embodiment.

Novel features that may be considered characteristic of the present disclosure are set forth in the appended claims. The disclosure itself, however, as well as a preferred mode of use, various objectives and advantages thereof, will best be understood by reference to the following detailed description of an illustrative embodiment when read in conjunction with the accompanying drawings. The functionality of various circuits, devices or components described herein may be implemented as hardware (including discrete components, integrated circuits and systems-on-a-chip 'SoC'), firmware (including application specific integrated circuits and programmable chips) and/or software or a combination thereof, depending on the application requirements.

Many traditional techniques for fatigue testing are often time intensive and therefore less attractive in a fast paced semiconductor manufacturing environment. The newer laser spallation based adhesion testing techniques may be deployable for use in semiconductor manufacturing in the future. However, these techniques may not be applicable to test fatigue related defects in semiconductor and packaging materials. These problems may be addressed by an improved system and method for fatigue testing. In an improved method and system for testing and analysis of a sub-critical fatigue crack growth in a semiconductor device, energy pulses in the form of a laser beam are repeatedly impinged on the semiconductor device to induce mechanical stress below a threshold within the semiconductor device. The repeated cycling of the mechanical stress maintained below the threshold provides a rapid fatigue testing technique, which is deployable in a semiconductor manufacturing environment.

According to one embodiment, in a method and system for evaluating sub-critical fatigue crack growth in a semiconductor device, a plurality of energy pulses generated by an energy source are repeatedly impinged onto the semiconductor device for a predefined time interval. The repeated impinging of the plurality of energy pulses induces a mechanical stress within the semiconductor device. The induced mechanical stress maintained below a threshold and repeated for a predefined number of cycles causes a formation of a sub-critical fatigue crack within the semiconductor device. A detector detects a presence of the sub-critical fatigue crack leading to a fatigue failure. A rapid determination of a pass or fail status for a fatigue test of the semiconductor device is made by comparing a total number of cycles to fatigue failure to a predefined benchmark.

Fatigue tests may be conducted to determine a relationship between a stress range and a number of times or cycles the stress may be applied before causing a fatigue induced failure in a specimen or device being tested. The type of stresses applied may include tension, compression, torsion and bending and/or a combination thereof. In many applications, semiconductor and packaging materials, which may be used to fabricate a semiconductor device, are subjected to various stresses caused by vibration, oscillation, temperature cycling and similar others. The behavior of materials under such load conditions differs from the behavior of the device under a static load. Since the semiconductor and packaging material is subjected to repeated load/stress cycles (causing fatigue) in actual use, semiconductor device manufacturers are often faced with predicting fatigue life for the device, which may be defined as the total number of cycles to failure under predefined loading conditions. Analysis and evaluation of test data obtained from fatigue testing may advantageously provide improved simulation/models to predict the in-service life of materials.

FIG. 1 illustrates a block diagram of a fatigue test system 100, according to an embodiment. In the depicted embodiment, an energy source 110 generates a plurality of energy pulses 140. In a particular embodiment, the energy source 110 is an infra-red, Q-switched, Nd:YAG laser operable to provide one or more laser pulses having an adjustable amplitude and/or an adjustable duration, e.g., pulse width. The energy source 110 generates the plurality of energy pulses 140, e.g., pulse beam of light, along a first axis 112. A first optical element 150, such as a focuser 152 in the form of a convex lens, is positioned along the first axis 112 to receive the plurality of energy pulses 140. The first optical element 150 collimates the plurality of energy pulses 140 and passes the collimated beam along a second axis substantially parallel to the first axis 112. Sequentially spaced along the second axis and disposed transverse thereto are a constraining layer 160, an energy absorbing layer 162, a substrate layer 164, and a sample material layer 166. In a particular embodiment, the substrate layer 164 and the sample material layer 166 may be used to fabricate a test sample and/or may be used in the fabrication of a semiconductor device 190 being tested (also referred to as a device under test 'DUT' 190). In an embodiment, the test sample may be a partially fabricated semiconductor device. Thus, the DUT 190 may refer to the test sample, the semiconductor device being tested, or may refer to a material used in the semiconductor fabrication and packaging of the semiconductor device. In an exemplary non-depicted embodiment, additional material layer(s) may be applied over the material of interest, such as the sample material layer 166. Hence, the layer of interest may not reside on the surface, but may be buried.

In a particular embodiment, the semiconductor device 190 is one of a microprocessor, a digital signal processor, a radio frequency chip, a memory and a microcontroller. In one embodiment, the sample material layer 166 is an organic polymer, e.g., a polyimide dielectric material. In a particular embodiment, the sample material layer 166 may not be in a form of a film or a layer but may exist in 3D geometric formations such as spheres (for e.g., a solder ball).

The collimated beam of the plurality of energy pulses 140 is incident upon the constraining layer 160. In a particular embodiment, the first optical element 150 includes the focuser 152, and collimates the laser beam between 100 micrometers and 4 millimeters in diameter. The constraining layer 160 is generally transparent to the plurality of energy pulses 140 thereby transferring the energy to the energy absorbing layer 162. Absorption of the laser beam by the energy absorbing layer 162 leads to a sudden expansion of the layer 162 which, due to the axial constraints of the assembly, e.g., the constraining layer 160 and the substrate layer 164, generates a compressive shock wave or pulse directed towards the substrate layer 164 and the sample material layer 166. The energy absorbing layer 162 may be composed of a variety of metallic materials such as gold, germanium or aluminum. The constraining layer 160 may be composed of solid water glass and may be between 5 micrometers and 100 micrometers thick.

The compressive stress pulse propagating through the substrate layer 164 is incident upon a selective portion 168 of the DUT 190, such as the interface between the substrate layer 164 and the sample material layer 166. A part of the compressive pulse is transmitted towards the sample material layer 166 and a part is reflected, thereby forming a tension pulse. The formation of the tension pulses as well as the compressive pulses induce mechanical stress within the selective portion 168 of the DUT 190, e.g., within the sample material layer 166. The repeated application of the mechanical stress, maintained below a threshold, for a predetermined number of cycles results in the formation of one or more sub-critical fatigue cracks within the sample material 166. Continued application of the mechanical stress continues to grow the one or more sub-critical fatigue cracks leading to a fatigue induced failure of the DUT 190. A detector 180 detects a presence of a sub-critical fatigue crack formed due to the mechanical stress within the DUT 190. Although the formation of the mechanical stresses are described in the context of formation of tensile stresses, the disclosure is also applicable to mixed-mode stresses, e.g., compressive, tensile and shear. In an exemplary, non-depicted embodiment, it may be possible to change test sample orientation relative to the energy source, and/or to modify the sample (addition of glass material of specific geometry and orientation) to induce mixed-mode stresses within the selective portion 168 of the DUT 190.

In a particular embodiment, an amount of energy transferred from the energy source 110 to the DUT 190 by the plurality of energy pulses 140 is controlled by a controller 170 controlling the amplitude and the duration of the plurality of energy pulses 140. In one embodiment, the duration may vary from approximately 3 nanoseconds to approximately 10 nanoseconds. By selecting a particular amplitude and duration, a predefined amount of energy may be transferred to the DUT 190, thereby inducing a controlled mechanical stress that is maintained below a threshold.

In one embodiment, the predefined amount of energy transferred is maintained at a substantially constant value during the repeated impinging of the plurality of energy pulses 140 onto the DUT 190, thereby resulting in inducing stress below the critical threshold that induces catastrophic adhesive failure. In another embodiment, an amount of mechanical stress induced within the DUT 190 may vary from a minimum level to a maximum level by correspondingly controlling the amplitude and/or the duration of the plurality of energy pulses 140.

As described earlier, laser spallation refers to a break up and/or removal of material by a laser beam. Unlike adhesion testing, which utilizes laser spallation to remove material, fatigue testing is best performed when the plurality of energy pulses to the DUT 190 is advantageously tuned, controlled or adjusted by the controller 170 to be below the threshold that removes material. That is, the amount of energy transferred is adjusted to be below a predefined threshold value such that the induced mechanical stress does not result in any substantial spallation or removal of the substrate layer 164 and/or the sample material layer 166 but does result in fatigue testing the selective portion 168 of the DUT 190. If the plurality of the energy pulses 140 continue to be impinged after an onset of the fatigue induced failure of the sample material layer 166 of the DUT 190 then further impinging may result in spallation of the material. A particular value of the threshold selected may vary depending on the particular type(s) of material(s) used to fabricate the DUT 190. Thus, the laser energy provided by the energy source 110 may be tuned for each type of material to deliver a sub-critical fatigue stress.

In a particular embodiment, the controller 170 may generate an energy pulse having duration of a few nanoseconds, representing one test cycle. Several hundreds or thousands of test cycles may be generated in approximately one second and over a million test cycles may be generated within approximately 60 minutes. In a particular embodiment, the plurality of energy pulses 140 are impinged onto the DUT 190 for a predefined time interval, such as less than or equal to approximately 60 minutes. The repeated impinging of the plurality of energy pulses 140 onto the selective portion 168 causes the sub-critical fatigue crack to grow within the predefined time interval, thereby enabling rapid fatigue testing of the DUT 190. Thus, the fatigue test system 100 is advantageously deployable in a semiconductor manufacturing environment enabling rapid fatigue testing of the DUT 190.

In a particular embodiment, a logic circuit 184 coupled to the detector 180 to determine whether the sub-critical fatigue crack is less than a predefined length. As described earlier, fatigue induced cracks are typically progressive and grow under the action of the repeated stress. The sub-critical crack may be initially less than the predefined length but may exceed the predefined length after the repeated application of the induced mechanical stress due to the impinging of the plurality of energy pulses 140. The logic circuit 184 may determine that the semiconductor device 190 is fatigued when the sub-critical fatigue crack is at least equal to the predefined length.

In one embodiment, a rapid determination of a pass or fail status for a fatigue test of the semiconductor device is made by comparing a total number of cycles to fatigue failure to a predefined benchmark. The particular value of the total number of cycles to fatigue failure selected may vary depending on the particular type(s) of material(s) used to fabricate the DUT 190. Thus, the test system 100 may be tuned for each type of material to rapidly test for fatigue failure. In addition, analysis and evaluation of test data obtained from the test system 100 may be advantageously used to improve simulation/models of fatigue testing of a particular material to predict the in-service life of the particular material.

A test event such as a fatigue failure may be determined to have occurred when a dimension of the displacement and/or the crack detected by the detector 180 is greater than a predefined benchmark or threshold. In a particular embodiment, the detector 180 used to detect a presence of the sub-critical fatigue crack formed within the DUT 190 may be based on various displacement and/or crack sensing technologies such as capacitance, acoustic emission, optical/visual and similar others. For example, for optically transparent materials, optical detection techniques may be deployed for detecting crack growth compared to a benchmark. In some applications, a change in capacitance may be utilized to detect a sub-critical crack. In a particular embodiment, the detector 180 may use optical properties, such those detectable by a charge coupled device (CCD) camera. In one embodiment, traditional interferometers and/or piezoelectric transducers may be used to detect displacement. In a particular embodiment, a broad band small detector (also referred to as a pinducer) may be mounted on the distal planes of the material being tested. The pinducer may be used to detect an acoustic emission from a spallation initiation event indicative of an occurrence of a fatigue failure.

In a particular embodiment, a feedback control signal 182 may be provided by the detector 180 to the controller 170. The feedback control signal 182 may be used to automatically control the amplitude and/or the duration of the plurality of energy pulses 140, thereby reducing the possibility of causing a substantial spallation of the sample material layer 166. For example, the controller 170 may stop the test system 100 during a test cycle when a fatigue failure is detected, and the particular test cycle inducing the fatigue failure is recorded. The controller 170 may automatically adjust amplitude and duration of the plurality of energy pulses 140 provided to another substantially similar specimen being tested in response to the previous fatigue failure test data.

Figure 2:
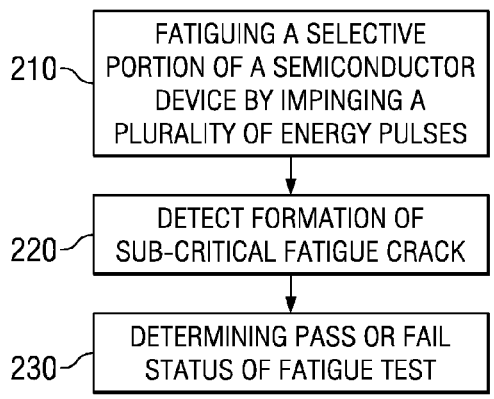
FIG. 2 is a flow chart illustrating a method of testing a semiconductor device, according to an embodiment.

FIG. 2 is a flow chart illustrating a method of testing a semiconductor device, according to an embodiment. At step 210, a selective portion of the semiconductor device is fatigued by impinging a plurality of energy pulses repeatedly onto the selective portion. In one embodiment, the selective portion of the semiconductor device is the sample material layer 166 of the DUT 190 and the plurality of energy pulses are the plurality of energy pulses 140. In a particular embodiment, an amount of energy included in the plurality of energy pulses impinged on the device is tuned or controlled to induce a mechanical stress below a threshold. At step 220, a presence of a sub-critical fatigue crack formed due to the impinging of the plurality of energy pulses for a predefined number of times within the selective portion is detected.

Various steps described above may be added, omitted, combined, altered, or performed in different orders. For example, an additional step may be added to determine a pass or fail status of a fatigue test. At step 230, a pass or fail status of a fatigue test of the semiconductor device may be determined by comparing a total number of cycles to fatigue failure to a predefined benchmark. For example, a particular material may experience fatigue failure in at least 100,000 cycles (defined as a benchmark). If the sub-critical fatigue crack exceeding a predefined benchmark is detected within 10,000 cycles then the specimen is declared to have failed the fatigue test.

Although illustrative embodiments have been shown and described, a wide range of modification, change and substitution is contemplated in the foregoing disclosure and in some instances, some features of the embodiments may be employed without a corresponding use of other features. Those of ordinary skill in the art will appreciate that the hardware and methods illustrated herein may vary depending on the implementation. For example, although the disclosure is described in the context of testing a semiconductor device, this disclosure is not limited to use with semiconductor devices; rather, it envisions use of a laser beam for rapidly fatigue testing any specimen to test fatigue failure. As another example, although the disclosure is described in the context of mechanical stresses caused due to tensile forces, the disclosure is equally applicable to mixed-mode stresses.

The methods and systems described herein provide for an adaptable implementation. Although certain embodiments have been described using specific examples, it will be apparent to those skilled in the art that the invention is not limited to these few examples. The benefits, advantages, solutions to problems, and any element(s) that may cause any benefit, advantage, or solution to occur or become more pronounced are not to be construed as a critical, required, or an essential feature or element of the present disclosure.

The above disclosed subject matter is to be considered illustrative, and not restrictive, and the appended claims are intended to cover all such modifications, enhancements, and other embodiments which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A test system for testing a test sample, the system comprising:
   an energy source to repeatedly impinge a plurality of energy pulses onto a selective portion of the test sample, wherein the plurality of the energy pulses induce a mechanical stress within the selective portion, wherein the mechanical stress induced is below a threshold; and
   a detector to detect a presence of a sub-critical fatigue crack formed within the selective portion due to the mechanical stress.

2. The test system of claim 1, comprising:
   a logic circuit coupled to the detector, wherein the logic circuit is operable to determine whether the sub-critical fatigue crack is less than a predefined length, wherein the test sample is fatigued when the sub-critical fatigue crack is at least equal to the predefined length.

3. The test system of claim 1, wherein the energy source is a Nd:YAG laser.

4. The test system of claim 1, wherein the plurality of energy pulses are repeatedly impinged for a predefined number of times, wherein the mechanical stress induced for the predefined number of times causes a fatigue failure within the selective portion.

5. The test system of claim 1, comprising:
   a controller included in the energy source, wherein the controller is operable to repeatedly impinge the plurality of energy pulses onto the test sample for a predefined time interval, wherein the predefined time interval is less than approximately 60 minutes.

6. The test system of claim 5, wherein an energy amount delivered by the plurality of energy pulses to the selective portion is substantially constant during the predefined time interval, wherein the plurality of energy pulses are repeatedly impinged for a predefined number of times thereby causing the sub-critical fatigue crack to grow within the predefined time interval to result in a fatigue failure.

7. The test system of claim 5, wherein the controller controls an amplitude and a duration of the plurality of energy pulses, wherein the mechanical stress induced within the test sample is maintained below the threshold by varying the amplitude and the duration of the plurality of energy pulses.

8. The test system of claim 1, wherein the presence of the sub-critical fatigue crack is detected by detecting a change in capacitance.

9. The test system of claim 1, wherein the presence of the sub-critical fatigue crack is detected by an acoustical signal.

10. The test system of claim 1, wherein the test sample is a semiconductor device, wherein the semiconductor device is one of a microprocessor, a digital signal processor a radio frequency chip, a memory and a microcontroller.

11. The test system of claim 1, wherein the mechanical stress is induced within a material used to fabricate the selective portion of the test sample.

12. The test system of claim 11, wherein the material is an organic polymer.

13. The test system of claim 1, wherein the presence of the sub-critical fatigue crack is detected by detecting a change in an optical property.

14. An apparatus comprising:
   an energy source to generate a plurality of energy pulses;
   a focuser to channel the plurality of energy pulses to impinge onto a selective portion of a test sample, wherein the plurality of the energy pulses induce a mechanical stress below a threshold within the selective portion and
   a controller to control, based on feedback from a detector capable of sensing a sub-critical fatigue crack in the test sample, the repeated impinging of the plurality of energy pulses onto the selective portion.

15. The apparatus of claim 14, wherein the test sample is a semiconductor device, wherein the semiconductor device is one of a microprocessor, a digital signal processor, a radio frequency chip, a memory and a microcontroller.

16. The apparatus of claim 14, wherein the energy source is a Nd:YAG laser.

17. The apparatus of claim 14, wherein the mechanical stress induced within the test sample is varied below the threshold by varying an amplitude and a duration of the plurality of energy pulses.

18. A method of testing a test sample, the method comprising:

fatiguing a selective portion of the test sample by impinging a plurality of energy pulses repeatedly onto the selective portion, wherein the impinging of the plurality of energy pulses induces a mechanical stress below a threshold; and detecting a presence of a sub-critical fatigue crack formed within the selective portion, the sub-critical fatigue crack being formed due to the impinging of the plurality of energy pulses for a predefined number of times.

19. The method of claim 18, wherein the test sample is a semiconductor device, wherein the semiconductor device is one of a microprocessor, a digital signal processor, a radio frequency chip, a memory and a microcontroller.

20. The method of claim 18, comprising:

determining a pass or fail status of a fatigue test of the test sample by comparing a total number of cycles to fatigue failure to a predefined benchmark.

* * * * *